United States Patent
Zang et al.

(10) Patent No.: US 11,900,541 B2
(45) Date of Patent: Feb. 13, 2024

(54) METHOD AND SYSTEM OF DEPTH DETERMINATION WITH CLOSED FORM SOLUTION IN MODEL FUSION FOR LAPAROSCOPIC SURGICAL GUIDANCE

(71) Applicant: EDDA TECHNOLOGY, INC., Princeton, NJ (US)

(72) Inventors: Xiaonan Zang, Princeton, NJ (US); Guo-Qing Wei, Plainsboro, NJ (US); Cheng-Chung Liang, West Windsor, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 14 days.

(21) Appl. No.: 17/745,600

(22) Filed: May 16, 2022

(65) Prior Publication Data
US 2022/0375173 A1 Nov. 24, 2022

Related U.S. Application Data

(60) Provisional application No. 63/188,625, filed on May 14, 2021.

(51) Int. Cl.
*G06T 17/20* (2006.01)
*A61B 34/10* (2016.01)
(Continued)

(52) U.S. Cl.
CPC .......... *G06T 17/20* (2013.01); *A61B 1/00009* (2013.01); *A61B 1/3132* (2013.01);
(Continued)

(58) Field of Classification Search
CPC .... G06T 7/0014; G06T 2200/04; G16H 10/65
See application file for complete search history.

(56) References Cited

U.S. PATENT DOCUMENTS

| | | |
|---|---|---|
| 2013/0060146 A1 | 3/2013 | Yang et al. |
| 2015/0302634 A1 | 10/2015 | Florent et al. |

(Continued)

OTHER PUBLICATIONS

Robu, Automatic registration of 3D models to laparoscopic video images for guidance during liver surgery, 04-040-2020, University College London, pp. 1-95 (Year: 2020).*

(Continued)

*Primary Examiner* — Samantha (Yuehan) Wang
(74) *Attorney, Agent, or Firm* — Venable LLP

(57) ABSTRACT

The present teaching relates to method, system, medium, and implementations for estimating 3D coordinate of a 3D virtual model. Two pairs of feature points are obtained. Each of the pairs includes a respective 2D feature point on an organ observed in a 2D image, acquired during a medical procedure, and a respective corresponding 3D feature point from a 3D virtual model, constructed for the organ prior to the procedure based on a plurality of images of the organ. The depths of the first and the second 3D feature points are substantially the same. A first 3D coordinate of the first 3D feature point and a second 3D coordinate of the second 3D feature point are automatically determined based on the pairs of feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

20 Claims, 5 Drawing Sheets

(51) Int. Cl.
    *G06T 19/20* (2011.01)
    *G06T 7/50* (2017.01)
    *G06T 7/33* (2017.01)
    *G06T 7/73* (2017.01)
    *A61B 1/00* (2006.01)
    *A61B 1/313* (2006.01)
    *G06T 7/80* (2017.01)
    *G06T 19/00* (2011.01)

(52) U.S. Cl.
CPC .............. *A61B 34/10* (2016.02); *G06T 7/344* (2017.01); *G06T 7/50* (2017.01); *G06T 7/75* (2017.01); *G06T 7/80* (2017.01); *G06T 19/006* (2013.01); *G06T 19/20* (2013.01); *A61B 1/00057* (2013.01); *A61B 2034/105* (2016.02); *G06T 2207/10016* (2013.01); *G06T 2207/10068* (2013.01); *G06T 2207/20092* (2013.01); *G06T 2207/30004* (2013.01); *G06T 2210/41* (2013.01); *G06T 2219/2004* (2013.01); *G06T 2219/2016* (2013.01)

(56) References Cited

U.S. PATENT DOCUMENTS

2017/0128145 A1   5/2017  Hasser et al.
2018/0071032 A1*  3/2018  de Almeida Barreto ...................
                                               G06T 19/006

OTHER PUBLICATIONS

Wang et al., Dynamic 2-D/3-D Rigid Registration Framework Using Point-To-Plane Correspondence Model, 2017, IEEE Transactions On Medical Imaging, pp. 1-16 (Year: 2017).*
International Search Report and Written opinion dated Sep. 29, 2022 in International Application No. PCT/US2022/29478.
International Search Report and Written opinion dated Sep. 29, 2022 in International Application No. PCT/US2022/29474.
International Search Report and Written opinion dated Sep. 29, 2022 in International Application No. PCT/US2022/29469.
Wang et al., "Dynamic 2-D/3-D Rigid Registration Framework Using Point-To-Plane Correspondence Model", IEEE Transactions on Medical Imaging, May 2017, pp. 1-16, vol. 36, Issue 9.
Robu, "Automatic registration of 3D models to laparoscopic video images for guidance during liver surgery", Dissertation: Medical Physics and Biomedical Engineering, University College London, Apr. 4, 2020, pp. 49-144.

* cited by examiner

METHOD AND SYSTEM OF DEPTH DETERMINATION WITH CLOSED FORM SOLUTION IN MODEL FUSION FOR LAPAROSCOPIC SURGICAL GUIDANCE

CROSS-REFERENCE TO RELATED APPLICATIONS

The present application claims priority to U.S. Provisional Patent Application No. 63/188,625, filed May 14, 2021, entitled "METHOD AND SYSTEM OF MODEL FUSION FOR LAPAROSCOPIC SURGICAL GUIDANCE", which is incorporated herein by reference in its entirety.

The present application is related to U.S. patent application Ser. No. 17/745,555, entitled "METHOD AND SYSTEM OF MODEL FUSION FOR LAPAROSCOPIC SURGICAL GUIDANCE", International Patent Application No. PCT/US2022/029469, entitled "METHOD AND SYSTEM OF MODEL FUSION FOR LAPAROSCOPIC SURGICAL GUIDANCE", International Patent Application No. PCT/US2022/029474, entitled "METHOD AND SYSTEM OF DEPTH DETERMINATION WITH CLOSED FORM SOLUTION IN MODEL FUSION FOR LAPAROSCOPIC SURGICAL GUIDANCE", U.S. patent application Ser. No. 17/745,518, entitled "METHOD AND SYSTEM OF DEPTH DETERMINATION IN MODEL FUSION FOR LAPAROSCOPIC SURGICAL GUIDANCE", and International Patent Application No. PCT/US2022/029478, entitled "METHOD AND SYSTEM OF DEPTH DETERMINATION IN MODEL FUSION FOR LAPAROSCOPIC SURGICAL GUIDANCE", all of which are incorporated herein by reference in their entireties.

BACKGROUND OF THE INVENTION

1. Field of the Invention

This invention generally relates to methods for aligning a virtual patient model to a real patient's video images and for providing continuously motion-tracked alignment in a laparoscopic environment during minimum invasive surgical procedures.

2. Description of Related Art

Minimum invasive surgery (MIS) has been utilized in numerous chest and abdominal surgical procedures. During MIS procedures, physicians often use an endoscope to provide a live 2D view of the anatomies inside the human body for surgical guidance. This type of scope, however, only provides a limited field of view, which in turn leads to a long learning curve for physicians to comprehensively correlate 2D video information with a pre-surgical 3D planning model to operate on regions of interest.

To address these shortcomings, image-guided system (IGS) has been developed to effectively overlay 3D virtual models and surgical plans onto 2D video images, and to accurately localize (i.e. find the position and orientation of) the laparoscopic camera in the 3D virtual patient space continuously during a surgical procedure. Because of the complexities due to, e.g., fast endoscope movements or blurred endoscopic images, physicians usually have to completely rely on manual operation to establish the initial alignment between a preoperative 3D model and 2D intra-operative video images. This interactive procedure, however, may be lengthy and disturb the surgical intervention. This is particularly so if this procedure requires a user to manually pick multiple pairs of corresponding landmarks between a 2D video image and a 3D model in the virtual patient space. This procedure may also require complicated mouse and keyboard maneuvers in order to adjust the transformation between a 3D virtual structure and a 2D image. Since the transformation is of 6 degrees-of-freedoms (DOFs), using mouse-based control to modify such a transformation may lead to high sensitivity and thus is not a trivial task. Therefore, there is a need to provide an effective method for aligning a preoperative 3D virtual model with a 2D patient image, and to provide motion-tracked alignment between the 3D virtual model and live laparoscopic images.

SUMMARY

The teachings disclosed herein relate to methods, systems, and programming for information management. More particularly, the present teaching relates to methods, systems, and programming related to hash table and storage management using the same.

In one example, a method, implemented on a machine having at least one processor, storage, and a communication platform capable of connecting to a network, is disclosed for estimating 3D coordinate of a 3D virtual model. Two pairs of feature points are obtained. Each of the pairs includes a respective 2D feature point on an organ observed in a 2D image, acquired during a medical procedure, and a respective corresponding 3D feature point from a 3D virtual model, constructed for the organ prior to the procedure based on a plurality of images of the organ. The depths of the first and the second 3D feature points are substantially the same. A first 3D coordinate of the first 3D feature point and a second 3D coordinate of the second 3D feature point are automatically determined based on the pairs of feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

In a different example, a system is disclosed for estimating 3D coordinate of a 3D virtual model. The system disclosed is constructed to include an anatomical structure mesh generation unit, a pre-operative key-pose generation unit, and a one-marker based model to video alignment unit. These different units operate together in accordance with the process as disclosed for estimating a 3D coordinate of a 3D virtual model by automatically determining the 3D coordinates of 3D feature points on the 3D virtual model so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

Other concepts relate to software for implementing the present teaching. A software product, in accordance with this concept, includes at least one machine-readable non-transitory medium and information carried by the medium. The information carried by the medium may be executable program code data, parameters in association with the executable program code, and/or information related to a user, a request, content, or other additional information.

Another example is a machine-readable, non-transitory and tangible medium having information recorded thereon for estimating 3D coordinate of a 3D virtual model. The information, when read by the machine, causes the machine to perform the following steps. Two pairs of feature points are obtained. Each of the pairs includes a respective 2D feature point on an organ observed in a 2D image, acquired during a medical procedure, and a respective corresponding 3D feature point from a 3D virtual model, constructed for the organ prior to the procedure based on a plurality of images of the organ. The depths of the first and the second 3D feature points are substantially the same. A first 3D coordinate of the first 3D feature point and a second 3D coordinate of the second 3D feature point are automatically determined based on the pairs of feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The inventions claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

Figure 1:
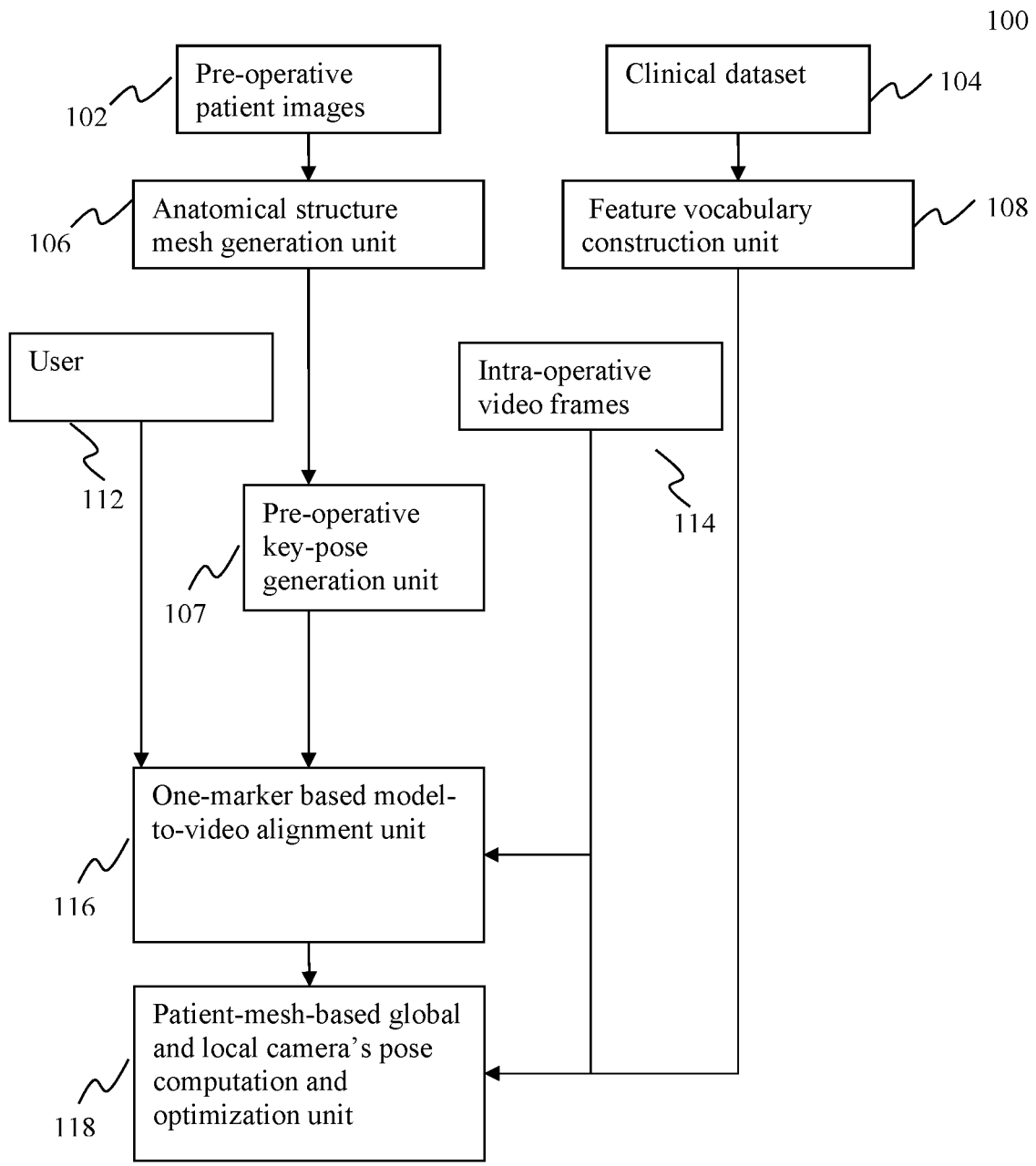
FIG. 1 shows an exemplary system diagram for aligning a virtual model with a real video frame and for providing motion-tracked alignment on laparoscopic video stream in accordance with various embodiments.

In the following detailed description, numerous specific details are set forth by way of examples in order to facilitate a thorough understanding of the relevant teachings. However, it should be apparent to those skilled in the art that the present teachings may be practiced without such details. In other instances, well known methods, procedures, components, and/or system have been described at a relatively high-level, without detail, in order to avoid unnecessarily obscuring aspects of the present teachings.

The present invention is generally directed to finding parameters to be used for overlaying the 2D projection of a 3D virtual model (including a surgical plan), constructed for an organ of a patient based on prior medical images of the patient, on 2D laparoscopic video images captured from the same patient in real time during a medical procedure. The 2D projection of the 3D virtual model needs to be substantially overlapping with the 2D boundary of the organ in a 2D laparoscopic video image. As the 3D virtual model in a virtual 3D space has 6 degrees of freedom (DOF), a particular 3D pose (in the 6 degrees of freedom) of the 3D virtual model needs to be determined in such a way that a projection of the 3D virtual model from this 3D pose to the 2D image plane yields the desired overlay that matches the visual appearance and size of the organ as observed in the 2D laparoscopic video image. In addition, as motion exists during a laparoscopic procedure, the overlay is dynamically changing over time in real time so that the 3D pose needs to be adaptively adjusted based on the continuously tracked motion during the procedure.

The present teaching discloses a method for projecting a 3D virtual model onto a 2D laparoscopic image plane to create a matched overlay. First, a key-pose may be generated. The key-pose represents an approximate position and orientation of the laparoscope with respect to the patient's organ. Such a key-pose may be generated pre-surgically based on the patient scans, such as CT or MRI. During the surgery, the key-pose may be retrieved and used to perform an initial rough overlay of the projection of the 3D virtual model onto the 2D laparoscopic image plane. The key-pose may be refined based on sequential steps to determine individual components of the translation and rotation parameters. Based on one pair of feature points (also called landmarks), the X-Y position of the feature point in the 2D laparoscopic image may be determined and the corresponding 3D feature point may be locked on the line of sight formed with respect to a laparoscopic camera. The depth (Z-coordinate) of the corresponding 3D feature point in the coordinate system of the laparoscopic camera is to be selected in such a way that the projection of the 3D virtual model from that depth onto the 2D image plane will yield the matching overlay. According to the present teaching, such desired depth may be determined interactively or automatically. Upon the X-Y-Z position of the corresponding 3D feature point is determined, the 3 remaining degrees of freedom related to the rotational components may be subsequently determined, either manually or automatically.

The 3D pose needed to project the 3D virtual model to create a desired matching overlay includes a 3D coordinate (X, Y, Z) of (a representative point on) the 3D virtual model. In some embodiments, the values of X and Y may be determined (up to an arbitrary scale factor) based on a pair of feature points. One of the feature points is selected from the 2D image of the patient's video data and the other is a corresponding feature point on the 3D virtual model. Then the value of Z of the 3D feature point may be determined using one of the two alternative approaches, according to the present teaching. This in turn determines the scale factor for the X and Y values. To facilitate both approaches, a second pair of feature points may be identified, with one from the 2D image and the other from the 3D virtual model. Each pair of feature points form a line of sight starting from the same focal point. There are two scenarios, depending on the two corresponding 3D feature points, and the Z value in each scenario may be determine using an alternative method.

In the first scenario, the two 3D feature points from the respective pairs have substantially the same depth. In this case, the depth or Z value of the 3D feature points on the 3D virtual model may be determined via a closed-form solution, i.e., based on a formulation of the distance between the two 3D feature points. That is, the depth value of the feature points on the 3D virtual model can be computed based on their relationship with the 2D coordinates of the corresponding 2D feature points in the 2D image and the 3D coordinates of the feature points in the 3D model.

When the depths of the two 3D feature points are not the same, an alternative approach can be used to determine the Z values of the 3D virtual model. In this scenario, the distance between two 3D feature points may be determined and used to identify a searching range along a line of sight for a desired Z or depth value, at which a projection of the 3D virtual model to the 2D image plane yields an object size that matches with that of the 2D object as observed in the 2D image. During the search, at each search point within the range along the line of sight, the 3D virtual model is projected onto the 2D image plane and the boundary/size of the projection may then be compared with the boundary/size of the organ observed in the 2D image plane. When the projected size and the observed size are substantially the same, the depth value at the search point from where the 3D virtual model is projected corresponds to the depth to be searched.

FIG. 1 shows an exemplary high level diagram of a system 100 for facilitating dynamic alignment between a 3D virtual model and an actual patient's 2D laparoscopic images based on motion tracked from a laparoscopic video stream, according to an embodiment of the current teaching. The system 100 includes, in one embodiment, an anatomical structure mesh generation unit 106, derived from preoperative patient images 102, a preoperative key-pose generation unit 107, a feature vocabulary construction unit 108, built upon collected clinical dataset 104, an one-marker based model-to-video alignment unit 116, a mesh-based global and local camera pose computation and optimization unit 118. In the illustrated embodiment, units 116 and 118 operate based on the intraoperative video frames 114.

The anatomical structure mesh generation unit 106 may be configured to generate a patient-specific organ mesh from pre-operative images, such as CT or MRI. The mesh includes a set of connected nodes, each of which is a 3D point inside the scanned patient data volume. The preoperative key-pose generation unit 107 may be configured to facilitate a user to maneuver a virtual laparoscope inside the 3D patient virtual space and preview the layout of anatomical structures at a pre-planned position and orientation (i.e., a key-pose) for the laparoscope. The key-pose represents the approximate laparoscope position and orientation with respect to the patient's 3D organ where the surgeon plans to begin to perform the surgery. The planned preoperative key-pose may be saved for future retrieval during the actual surgery.

The feature vocabulary construction unit 108 is provided to build a set of clinical image features from laparoscopic video streams which may be recorded during various chest and abdominal surgical procedures. Such clinical image features may be stored in a database, which may include a set of image features showing significant anatomical landmarks. The content stored in this database may then be used as a vocabulary of features to facilitate detection and recognition of similar image features extracted from laparoscopic video frames during a MIS procedure. For example, laparoscopic images that show falciform ligament and anterior ridge line of a liver may be saved in the database as part of feature vocabulary. Subsequently, during a MIS procedure performed on the liver, the system may automatically recognize extracted image features as the falciform ligament of a liver. Accurate recognition of anatomical features from images may facilitate to optimize the initial estimation of the key pose, i.e., the position and orientation of a laparoscopic camera, and enable a continuously computation of the camera's poses.

During a procedure, a user 112 (such as a medical personnel) may interact with the one-marker based model-to-video alignment unit 116 to register an relevant virtual patient model with the laparoscopic image of the actual patient. The patient-mesh-based global and local camera's pose computation and optimization unit 118 may search through the feature vocabulary, retrieved from unit 108, to recognize relevant image features in order to optimize the initial position and orientation of the laparoscopic camera. The unit 118 may also continuously compute the laparoscopic camera's pose to enable a motion-tracked virtual patient model overlay onto live laparoscopic video images.

The system 100 may further include one or more peripheral input devices operated by user 112 such as a computer mouse, a keyboard, a stylus, one or more sensors, 3D manipulation gloves, or any other suitable input device, or any combination thereof. Furthermore, system 100 and/or any of the input devices may also correspond to a standalone device, such as, but not limited to, a mobile device (e.g., a smart phone, tablet, personal digital assistant, laptop, etc.), or a computing device (e.g., desktop computer, camera, etc.). The system may also include one or more processor, memory, communications circuitry, and a display, amongst other features. The processor(s) may include any suitable processing circuitry capable of controlling operations and functionality of the system. In some embodiments, the processor(s) may include a central processing unit ("CPU"), a graphic processing unit ("GPU"), one or more microprocessors, a digital signal processor, or any other type of processor, or any combination thereof. In some embodiments, the functionality of the processor(s) may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, the processor(s) may include their own local memory, which may store program systems, program data, and/or one or more operating systems. However, the processor(s) may run an operating system ("OS"), and/or one or more firmware applications, media applications, and/or applications resident thereon. In some embodiments, the processor(s) may run a local client script for reading and rendering content received from one or more websites. For example, the processor(s) may run a local JavaScript client for rendering HTML or XHTML content.

The memory may include one or more types of storage mediums such as any volatile or non-volatile memory, or any removable or non-removable memory implemented in any suitable manner to store data. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any combination thereof. Furthermore, the memory 304 may be implemented as computer-readable storage media ("CRSM"), which may be any available physical media accessible by the processor(s) to execute one or more instructions stored within the memory.

The communications circuitry may include any circuitry allowing or enabling one or more components of the system to communicate with one another, and/or with one or more additional devices, servers, and/or systems. In some embodiments, the communications circuitry may facilitate communications across a network, such as the Internet. For example, the communications circuitry may access the network(s) using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications. In some embodiments, a web browser using HTTP may be used for communications. Various additional communication protocols may be used to facilitate communications may include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP.

The display may, in one embodiment, may be any suitable type of display in communication with one or more of the processor(s), memory, and/or communications circuitry. Various types of displays may include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Still further, a touch screen may, in some embodiments, correspond to a display device including capacitive sensing panels capable of recognizing touch inputs thereon. In some embodiments, the display may be an optional component.

Figure 2:
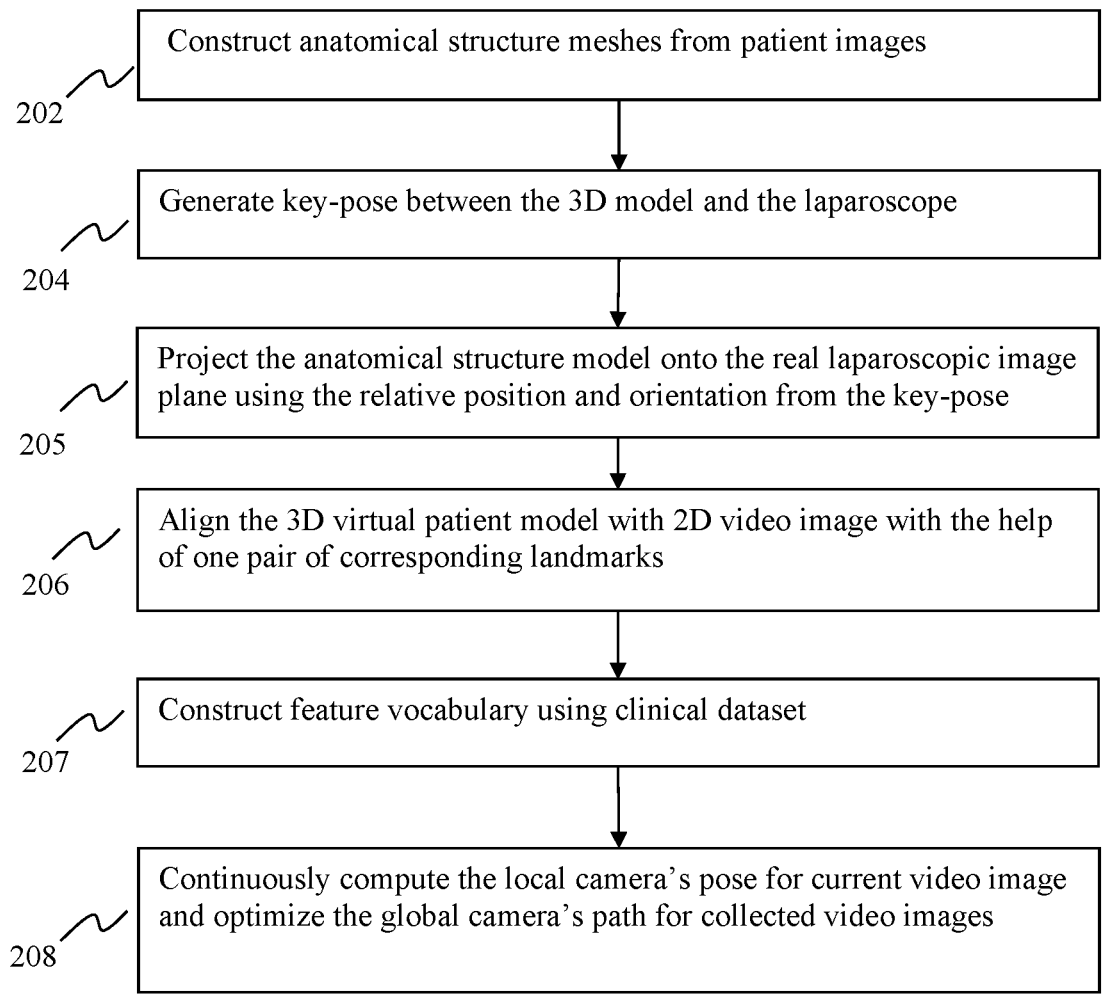
FIG. 2 illustrates an exemplary flow diagram for registering a virtual model to a real patient's laparoscopic image and for generating a continuous overlay onto live endoscopic video images in accordance with various embodiments.

FIG. 2 is a flowchart of an exemplary process for aligning a 3D virtual model with a real patient's laparoscopic video, according to one embodiment of the present teaching. At step 202, the 3D virtual model may be constructed by generating anatomical structure meshes based on pre-operative patient images. The construction may be automatic or semi-automatic. The patient images may be CT or MRI, or any other modalities. At step 204, one or more key-poses may be generated. Each key-pose defines a specific relative position and orientation between the anatomical structure meshes and a virtual laparoscope and approximates a position and orientation of the laparoscope during a surgery. A key-pose may be generated in an interactive procedure where a user may manually adjust the pose of a virtual laparoscope through an interactive device such as a computer mouse. A determined key-pose may then be saved for later fast retrieval during surgery.

At step 205, the patient's 3D anatomical structure model may be projected onto a real laparoscopic image based on the relative position and orientation of a selected key-pose. For each surgical procedure, a key-pose corresponding to the current surgical position may be retrieved from multiple key-poses generated previously and stored. Through the projection, the 3D anatomical structure model may be overlaid onto a real laparoscopic image. At step 206, a pair of corresponding landmarks or feature points on the 2D image and the 3D virtual model are identified and used to align the 3D virtual model with the 2D video image. Such feature points may be identified manually or automatically. In some embodiments, a user may click, using a mouse, the two corresponding points on the 2D video image and on the 3D virtual model, respectively. In other embodiments, a computer program may be used to automatically detect these same two feature points from the 2D image and 3D virtual model, respectively.

The laparoscope's camera coordinate system may be defined as follows: the horizontal span from left to right of the laparoscope's image plane is defined as the X-axis; the vertical span from top to bottom of the image plane is defined as the Y-axis; and the Z-axis is along the viewing direction (or line of sight) of the laparoscope. The coordinate origin is at the camera's center (also called the focal point). According to the present teaching, based on the one pair of corresponding feature points, one from the 2D image plane and the other from the 3D virtual model, the 3D coordinate of the corresponding feature point on the 3D virtual model can be computed (up to an arbitrary scale factor, see more detailed discussion below). Details of the relationship between a pair of corresponding 2D and 3D feature points (i.e., the relationship between the coordinate of a 2D feature point in the 2D image and that of a corresponding 3D feature point on the 3D virtual model) is disclosed in detailed below.

As discussed herein, projecting a 3D virtual model onto a 2D image plane, it involves six degrees of freedom, including X, Y, Z, as well as pitch, yaw, and roll that are rotations with respect to each of the three axes. In some embodiments, the estimation of pitch, yaw, and roll may be determined after the X, Y, and Z values are determined. In some embodiments, the key-pose may merely approximate a pose with a position and an orientation. The overlay achieved by projecting the 3D virtual model at a 3D coordinate with X, Y, Z values may not yield a perfect alignment between the projection and the 2D laparoscopic image. For example, the 3D virtual models may need to be rotated and fine-tuned with respect to any of the three axes in order to yield a projection that matches accurately with the corresponding 2D object image in the image plane. That is, the other degrees of freedom also need to be estimated with respect to the 3D virtual model in order to refine the alignment between the projection of the 3D virtual anatomical model and the 2D observation of the corresponding organ that the 3D virtual model represents in a patient's laparoscopic image.

At step 207, the feature vocabulary construction unit 108 may be provided to build a feature vocabulary. Note that a feature vocabulary may be updated based on incoming laparoscopic video images. For example, during a MIS procedure on a liver, a live laparoscopic video image may display the falciform of the liver. The image feature related to this falciform feature may be first recognized in the feature vocabulary because its feature description may be similar to the ones categorized as the liver falciform. Subsequently, the falciform image features, which are newly extracted from live laparoscopic video images, may be saved back into the feature vocabulary to provide an updated feature vocabulary, and grouped under the liver falciform category.

At step 208, different features may be extracted continuously from a given laparoscopic video image and such extracted features may be matched against the features stored in the feature vocabulary. A laparoscopic camera's pose may then be computed for the given image. That is, extracting image features, comparing with stored features in the feature vocabulary, and computing the camera's pose may be carried out for each of the video frames in the laparoscopic video stream. Any detected feature from each frame that do not match any existing features stored in the feature vocabulary may be either added into the feature vocabulary as a new category or filtered out as an outlier. Based on an estimated laparoscopic camera's pose with respect to a current video frame, the 3D virtual model may be projected onto the current video frame. In some embodiments, the features extracted from the 2D video frames may be associated with corresponding 3D nodes of the patient-specific anatomical meshes. Finally, a global optimization may be performed to adjust the entire camera movement trajectory and the 3D patient meshes. In some embodiments, tasks to be performed at step 208 may be executed in a parallel processing scheme to enhance the overall rea time processing speed.

Figure 3:
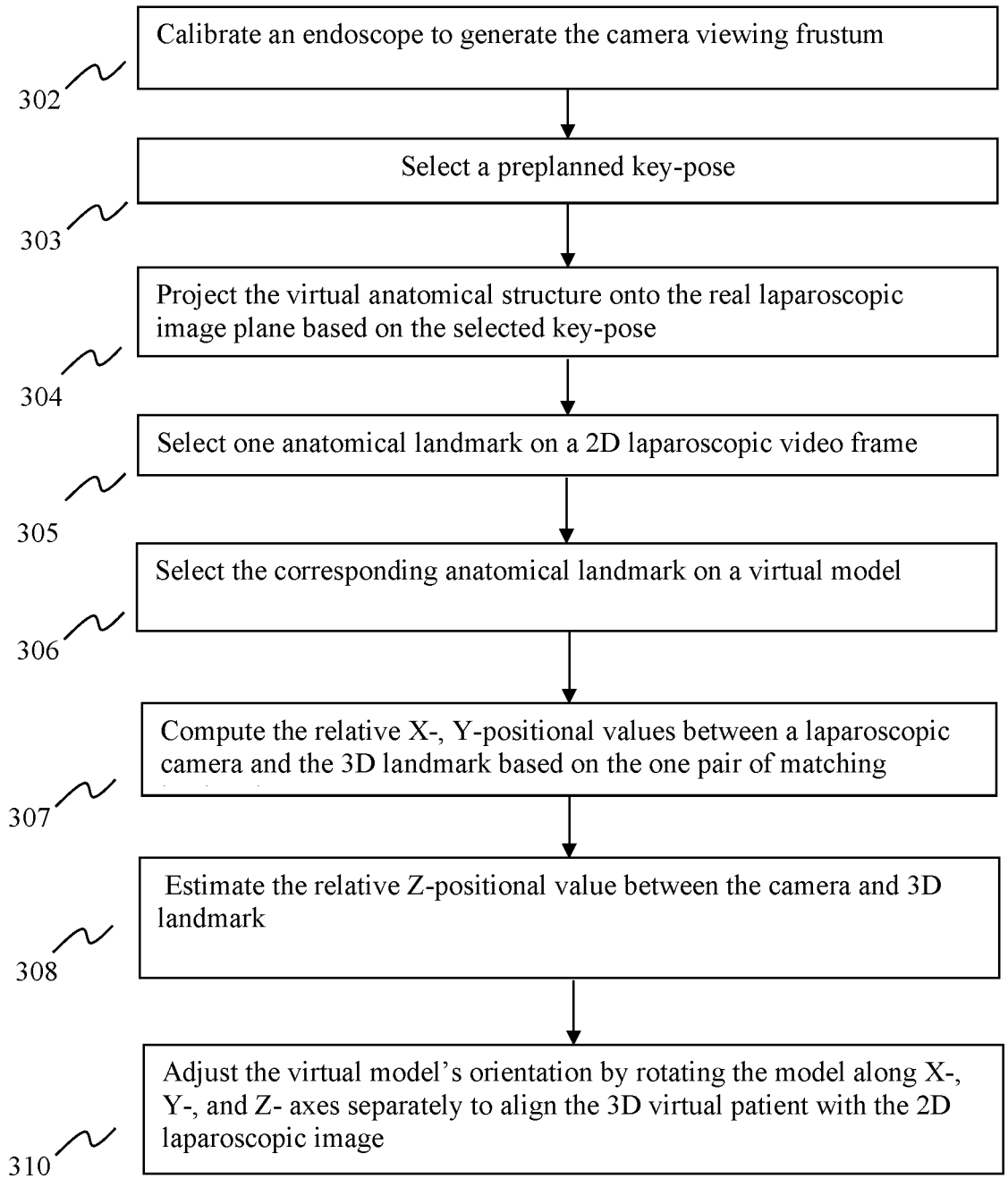
FIG. 3 illustrates an exemplary flow diagram of the interactive registration between a virtual model and endoscopic video images in accordance with various embodiments.

FIG. 3 is an exemplary flowchart of an exemplary process for the one-marker based model-to-video alignment unit 116, according to one embodiment of the present teaching. At step 302, the laparoscope may be calibrated to obtain certain camera parameters, such as focal lengths and principal point position. These parameters may be used to generate a camera viewing frustum so that only anatomical structures within the viewing frustum may be visible. Such parameters may also be used to generate a virtual laparoscopic image by rendering the 3D model in a perspective view port corresponding to the calibrated laparoscope. To visualize, in some embodiments, a first window for showing the rendered view of the 3D virtual model and a second window for displaying endoscopic video images may be provided side-by-side. At step 303, a user may select a pre-planned key-pose that corresponds to the current laparoscope's surgical position. At step 304, the 3D virtual anatomic structure or model may be projected onto the actual laparoscope image plane based on the calibrated laparoscope parameters as well as the relative position and orientation associated with the key-pose. The projection may result in an overlay of the 3D model onto the real 2D laparoscopic video image to generate a fused view of both the 3D model and 2D laparoscopic image in a single view. At step 305, a user (e.g., a medical professional) may select one anatomical landmark or 2D feature point in the laparoscopic video image. For example, a user may select the top intersecting position between the inferior vena cava (IVC) and liver. At step 306, the user may identify the corresponding landmark or 3D feature point in the 3D virtual space via, e.g., a mouse clicks. The input mouse position may be interpreted as the origin of a ray and the selected 3D landmark point is the intercepting point where this ray casts upon the organ surfaces (IVC and liver). Upon that the user corresponds the 3D landmark point in the virtual space with the selected 2D landmark point on a laparoscopic video image, the system may compute, at step 307, the X- and Y-positional translation (up to an arbitrary scale factor, which is the Z-position) between the 3D model and the laparoscopic camera system. In one embodiment, the X and Y positional values may be computed based on the Z-positional value in the key-pose, and the Z-positional value of the 3D landmark may be kept the same as that in the key-pose. Z-positional value of the 3D landmark will later be further refined.

Figure 4:
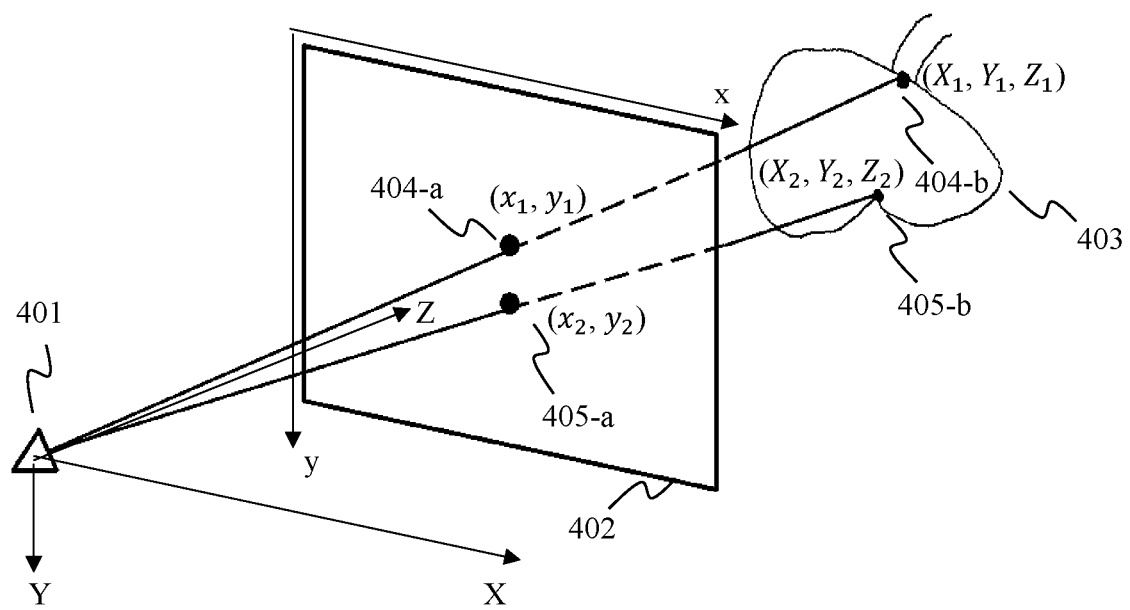
FIG. 4 shows an exemplary illustration for determining the position of a virtual model in a laparoscopic camera in accordance with various embodiments.

FIG. 4 illustrates an example of the laparoscopic imaging process and corresponding 2D and 3D feature points. In this figure, 401 represents the origin of the laparoscopic camera coordinate system, 402 is the 2D imaging plane, 403 is the 3D virtual model for an anatomical organ. The pair of points marked as 404-a and 404-b are the user-selected 2D landmark feature point (404-a) and the corresponding 3D landmark feature point (404-b), respectively. A line connecting origin point 401 and the 2D feature point 404-a forms a line of sight. Since 404-a and 404-b are corresponding feature points, the 3D virtual model 403 may be positioned from the key-pose in such a way that 404-b lies on the line of sight. Since 404-b can be on any point on the line of sight, the exact location of 404-b, and hence the 3D virtual model, along the line of sight needs to be determined in order for the projection of the 3D virtual model to match the organ observed in the 2D image.

Via the example shown in FIG. 4, it can be further illustrated how to compute the X- and Y- positional translation of a 3D landmark feature point in the laparoscopic camera coordinate system based on known coordinate of a 2D landmark point in a 2D image plane. Suppose (x,y) is the coordinate system of the image plane and (X,Y,Z) is the laparoscopic camera coordinate system. Assume that $(x_1, y_1)$ is the coordinate of a 2D landmark feature point in a 2D image plane. An example is shown in FIG. 4, where 2D feature point 404-a is a 2D feature in 2D image 402. Assume further that $(X_1, Y_1, Z_1)$ is the 3D coordinate of the corresponding 3D feature point in the 3D space with respect to the laparoscopic camera coordinate system. An example of such a 3D feature point is 404-b in FIG. 4, which corresponds to the 2D feature point 404-a. As discussed herein, when the corresponding 3D feature point is identified from the 3D virtual model 403, its 3D coordinate or $(X_1, Y_1, Z_1)$ in the camera coordinate system is restricted to be on the line of sight (the line between 401 and 404-b). When the 3D feature point (e.g., 404-b) is moving along the line of sight, its 3D coordinate changes accordingly, i.e., the values of $Z_1$, $X_1$, and $Y_1$ all change. However, because the 3D feature point is still on the line of sight despite the moves, its projection onto the 2D image (e.g., 402) remains at the same coordinate $(x_1, y_1)$ on the image plane 402. The following equation describes the relationship between the 2D coordinate of a feature point in the image coordinate system and the 3D coordinate of a corresponding 3D feature point in the camera coordinate system:

$$\begin{bmatrix} X_1 \\ Y_1 \\ Z_1 \end{bmatrix} = M_{camera} \begin{bmatrix} x_1 \\ y_1 \\ 1 \end{bmatrix} \cdot s_1$$

where $M_{camera}$ is a 3×3 matrix representing camera parameters obtained via camera calibration, $s_1$ is a scaling factor, which may be implicitly correlated with the distance from the 3D feature point to the image plane. As such, this distance corresponds to depth $Z_1$ that is sought here. Therefore, once depth $Z_1$ is determined, $X_1$ and $Y_1$ can be computed based on this formular.

Therefore, based on a pair of corresponding feature points in the 2D image plane and on the 3D virtual model, the X-, Y-positional values of the 3D landmark feature point may be computed at 307. That is, the 2D landmark feature point 404-a may now be used as an anchor point, despite of the positional changes of the 3D feature point so long as it is on the line of sight. At this step, as one embodiment, the Z-value may be assumed to be the same as that in the key-pose. Therefore, X-Y values are determined based on the Z-value in the key-pose. That is, the Z-value in the key-pose is assigned to $s_1$. The final Z-value may be estimated in the below step.

At step 308, a relative Z-axis translation of the 3D virtual model with respect to the laparoscopic camera may be estimated. The goal is to determine a scale factor or depth Z so that projection of the 3D virtual model at that depth will be able to match with the organ object image observed in the 2D image plane. According to the present teaching, this is achieved by using another pair of corresponding feature points, one from the 2D image plane and the other corresponding one is from the 3D virtual model. In one embodiment, a user may select another pair of feature points as the second pair of corresponding feature points. For example, the user may select the endpoint of a liver's falciform from the 2D laparoscopic video image and the 3D virtual model in the 3D virtual space. An example of the second pair is shown in FIG. 4, labeled as 405-$a$ and 405-$b$, respectively.

As discussed herein, there are two alternative methods to determine the value of Z (or scale factor s1) based on two pairs of landmark feature points. The first method supports a closed-form solution for computing the Z value, under the assumption that the two corresponding 3D feature points from the two pairs have substantially the same depth or Z value. The second method allows an estimation of the Z value via a different approach (as described below) when it cannot be assumed that the depths of the two corresponding 3D feature points are substantially equal. The two alternative methods of determining the Z value are respectively disclosed below based on the example shown in FIG. 4.

When two 3D feature point 405-$b$ is close to 404-$b$, it is reasonable to assume that the depth of 405-$b$ is substantially the same as that of point 404-$b$. If $(x_1, y_2)$ is the coordinate of feature point 405-$a$ in the 2D image plane 402, then, the 3D coordinates of the corresponding 3D feature point 405-$b$ in the laparoscopic camera system may be expressed as $$\begin{bmatrix} X_2 \\ Y_2 \\ Z_2 \end{bmatrix} = M_{camera} \begin{bmatrix} x_2 \\ y_2 \\ 1 \end{bmatrix} \cdot s_1$$

Denote the distance between the two 3D landmark feature points 404-$b$ and 405-$b$ as d, which is known as it can be determined from the known 3D virtual model). This distance may be expressed as $$d = \left\| \begin{bmatrix} X_1 \\ Y_1 \\ Z_1 \end{bmatrix} - \begin{bmatrix} X_2 \\ Y_2 \\ Z_2 \end{bmatrix} \right\|$$

where $\|.\|$ represents the Euclidean distance. Plugging in the expression for the 3D coordinates for 404-$b$ and 405-$b$, respectively, into the above equation, the distance may be obtained via the following equation:

$$d = \left\| M_{camera} \left( \begin{bmatrix} x_1 \\ y_1 \\ 1 \end{bmatrix} - \begin{bmatrix} x_2 \\ y_2 \\ 1 \end{bmatrix} \right) \right\| \cdot s_1$$

From this closed-form solution, the depth value, which is equal to the scale factor $s_1$ for the 3D landmark feature points 404-$b$ and 405-$b$ may be computed. That is, this scale factor corresponds to the Z-translational value representing the depth of the 3D virtual model and at this Z depth, a projection of the 3D virtual model will yield an overlay on the 2D image plane that matches better in size with that of the organ observed in the 2D image when compared with the Z value in the key-pose. With the computed Z value, the three translational components are determined.

In some situations, the depth of 405-$b$ may not be assumed to be substantially the same as that of point 404-$b$. In this situation, an alternative approach is disclosed to determine the scale factor or the depth of the 3D virtual model so that the projection of the 3D virtual model at that depth yields an overlay with the organ image that matches in size with that of the organ observed in the 2D image. With this approach, the estimation of the Z value may be achieved via semi-automatic operation and a determination may be made based on visual cues created while overlays are displayed based on projections at depths within a range determined automatically based on the two pairs of feature points. During this process, each of the projections may result in a visual observation of the size of the projected 3D model and it may be visually compared with the size of the organ observed in the real laparoscopic image. When the visual cues indicate a good match in size, the corresponding depth associated with the projection may be used as the desired depth.

Figure 5:
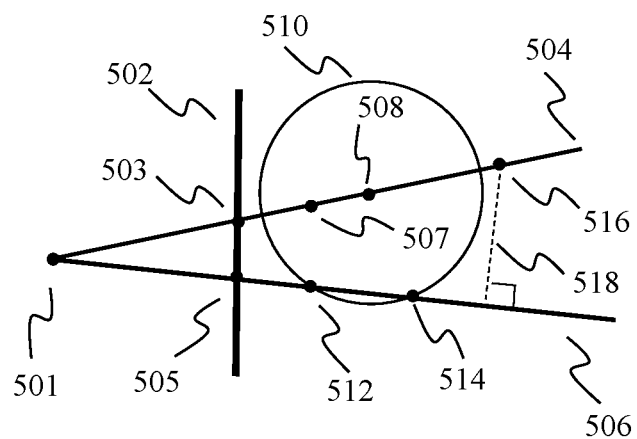
FIG. 5 illustrates an exemplary procedure to determine the depth value of a landmark.

FIG. 5 illustrates the automated approach to determine a range of depth in searching for an estimate of the Z value, according to an embodiment of the present teaching. In FIG. 5, 501 is the center of the laparoscopic camera, 502 is the image plane, 503 is the 2D landmark feature point from the first pair of feature points, 504 is the line of sight associated with the 2D feature point 503, 505 is the 2D landmark feature point from the second pair of feature points, and 506 is the line of sight associated with the 2D feature point 505. As discussed above, d is the known distance between the two 3D landmark feature points computed based on the 3D virtual model. Let the accuracy in estimating the depth value for the 2D landmark feature point from the first pair (i.e., point 503) is specified by parameter δ. Assume the depth value associated with the landmark feature point 503 is known not smaller than a minimum depth value D. For example, in FIG. 5, 507 may represent the point of a minimum depth in estimating the depth for 2D feature point 503. From point 507 along the line of sight 504 (from left to right), with an incremental step measured by δ, a circle with radius d may be drawn. One example shown in FIG. 5 is point 508, which is possibly advanced several times from the minimum depth point 507 on a line of sight 504, that serves as the center of a circle 510 with radius d. Although a circle is illustrated in FIG. 5 for illustration in 2D, the actual operation is in a 3D space. In that case, a sphere may be used instead.

At each of the incremental position of the line of sight 504 (incremented with step value δ), the perimeter/surface of the circle/sphere centered on the line of sight 504 intersects with the line of sight 506 associated with the other 2D feature point 505 from the second pair of feature points. For example, the circle centered at 508 on the line of sight 504 intersects with the line of sight 506 at two points 512 and 514. The distances from 508 to 512, and from 508 to 514 are all the same, which is the radius d. That is, within a certain incremental range, a circle centered at a point on the line of sight 504 may intersect at two separate positions with the line of sight 506 associated with the 2D feature point from the second pair. That is, there are two points on the line of sight 506 that has the same distance d to the center point of the circle on the line of sight 504.

When moving point 508 further along the line of sight 504 (of the 2D feature point of the first pair) from left to right, it will eventually encounter a point on the line of sight 504 whose distance to the second line of sight 506 is exactly d and at that point, the circle centered at this point intersects the second line of sight 506 at only one point. FIG. 5 provides such an example, where point 516 on the line of sight 504 is the center of a circle that intersect the line of sight 506 at one point on 506 and the distance between 516 and the line of sight 506 is d. This indicates that beyond 516, a circle centered at a point on the line of sight 504 with radius d will no longer intersect with the second line of sight 506. Thus, point 516 represents a point of maximum depth value. As such, the desired depth value Z is between a minimum depth value associated with point 507 and a maximum depth value associated with point 516. In this way, a range of possible depth values is determined.

With the range for the possible depth values automatically determined, a specific depth Z value may be identified from this range via a process of projection and visual inspection. At each of all possible depth values within the range, the 3D virtual model is projected, from the current depth position on the line of sight (e.g., 504), onto the 2D image plane to create an overlay with the corresponding organ observed in the 2D image. As at this stage, the orientation of the 3D virtual model is still not yet determined (which is an approximate value in the key-pose), an assessment on quality of matching may be computed based on, e.g., the difference between the size of the 3D virtual model when projected onto the image plane and the 2D size of the organ as observed in the real laparoscopic image. The assessment may be performed based on either some automatically generated relevant metric or user visual inspection. The automatically generated metric may be computed to reflect a discrepancy in overall size difference without factoring in the different in shape. For instance, a bounding box may be created for the observed organ in the 2D image and the same can be done for the projected 3D virtual model. The difference in areas of the two bounding boxes may be used to estimate the size difference. The depth value that yields the smallest size difference may be selected as the desired depth. Another way to assess the similarity between the size of the projection of the 3D virtual model at a certain depth and the size of the organ as observed in the 2D image. In this mode of operation, a user observed the overlay and selects the one that looks most matching in size with the actual observed organ in the 2D image.

Once the depth value is determined, three out of six degrees of freedom has been determined according to the different alternative methods of the present teaching. The remaining three degrees of freedom may be determined by, e.g., adjusting the orientation of the 3D virtual model so that the projection on the 2D image plane is aligned with the observed real anatomical structures observed from the endoscopic video frame. This is achieved at step 310. The user may change the orientation of the 3D virtual model by manually adjusting the relative X-, Y-, and Z-rotations with respect to the first pair of 2D/3D matched landmark points. In some embodiments, such manipulations may be achieved through mouse maneuvers. For example, user may rotate the 3D virtual model with respect to the laparoscope's Z-axis by pressing down the left mouse button and moving the mouse around. In other embodiments, the user may also adjust the orientations of the 3D virtual model around laparoscope's X- and Y-axes by holding down the right mouse button and then moving the mouse around.

In some embodiments, user's visual inspection may be applied to make an assessment as to whether the shape of the projected 3D model aligns with the shape of the anatomical structure observed in the 2D video image. The user may select a specific combination of X-, Y-, Z-rotations that yields the most visually satisfactory alignment. Alternatively, a computer program may be provided to, e.g., automatically use different X-, Y-, and Z-rotation combinations (e.g., exhaustively) and compute a matching quality measure for each combination indicating the degree of matching between the projected 3D virtual model and the boundary of the corresponding anatomical structure observed in the 2D image and then a best combination is determined that yields the best matching quality measure.

Upon all six degrees of freedom in translation and rotation are determined to derive a matched overlay, a user may continue to adjust manually each of the translation values as well each of the rotation angles with respect to the 3D model. Some adjustments may also be applied to the real laparoscopic image. Such manual manipulation may be through any peripheral devices such as a mouse or joystick or keyboard control to achieve an alignment as desired by the user who is using the overlay in a real time scenario during the laparoscopic procedure in order to achieve certain medical purpose.

The above-described process and system set up are for accurately overlaying a 3D virtual model constructed using previous medical images prior to a medical procedure such as a laparoscopic procedure on to an 2D laparoscopic image acquired during the medical procedure. Examples used in describing the concepts and steps are for illustration purpose only and they are not intended as limitation to the present teaching. Different steps and operations as discussed herein may be implemented using different means. For example, in performing any step as described herein, based on parameter values obtained by a computer during the process as disclosed, a user may manually step in to adjust such parameter values. As another example, the order of some of the steps to carry out the process of determining the translation and rotation components may also be different as needed. These design choices or variations are all within the scope of the present teaching.

We claim:

1. A method implemented on at least one processor, a memory, and a communication platform for estimating a three-dimensional (3D) coordinate of a 3D virtual model, comprising:
   accessing a 3D virtual model constructed for an organ of a patient based on a plurality of images of the organ prior to a medical procedure;
   obtaining a first pair of corresponding feature points, with a first two-dimensional (2D) feature point on the organ observed in a 2D image acquired during the medical procedure and a first corresponding 3D feature point from the 3D virtual model;
   obtaining a second pair of corresponding feature points, with a second 2D feature point on the organ observed in the 2D image and a second corresponding 3D feature point from the 3D virtual model, wherein the depths of the first and the second 3D feature points are substantially the same; and
   automatically determining a first 3D coordinate of the first 3D feature point and a second 3D coordinate of the second 3D feature point based on the first and the second pairs of corresponding feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

2. The method of claim 1, wherein
the 3D virtual model has six degrees of freedom with first three degrees of freedom related to the 3D coordinate having values along X, Y, Z axes of a camera coordinate system; and
a depth corresponding to Z value of the 3D coordinate is on a line of sight of the first 2D feature point that has a 2D coordinate with respect to an image coordinate system.

3. The method of claim 2, wherein the 3D virtual model has second three degrees of freedom related to rotations of the 3D virtual model with respect to each of the X, Y, and Z axes.

4. The method of claim 2, wherein the line of sight is formed between the first 2D feature point and a focal point of a camera associated with a medical instrument deployed in the medical procedure.

5. The method of claim 2, wherein the first 3D coordinate of the first 3D feature point and the second 3D coordinate of the second 3D feature point are determined based on:

$$\begin{bmatrix} X_1 \\ Y_1 \\ Z_1 \end{bmatrix} = M_{camera} \begin{bmatrix} x_1 \\ y_1 \\ 1 \end{bmatrix} \cdot s_1$$

$$\begin{bmatrix} X_2 \\ Y_2 \\ Z_2 \end{bmatrix} = M_{camera} \begin{bmatrix} x_2 \\ y_2 \\ 1 \end{bmatrix} \cdot s_1$$

where $(X_1, Y_1, Z_1)$ and $(X_2, Y_2, Z_2)$ are respectively three values along X, Y, Z axes for the first and the second 3D coordinates, $(x_1, y_1)$ and $(x_2, y_2)$ are respectively the image coordinates of the first and the second 2D feature points, and $s_1$ is a scaling factor along the line of sight corresponding to depth Z, which, when the first and the second 3D feature points have substantially the same depth, can be solved from $$d = \left\| M_{camera} \left( \begin{bmatrix} x_1 \\ y_1 \\ 1 \end{bmatrix} - \begin{bmatrix} x_2 \\ y_2 \\ 1 \end{bmatrix} \right) \right\| s_1$$

where d on the left side represents the second distance and the expression on the right side represents the first distance and $M_{camera}$ is a matrix representing camera parameters obtained via camera calibration.

6. The method of claim 3, further comprising determining the second three degrees of freedom via:
adjusting rotation of the 3D virtual model with respect to at least one of the X, Y, and Z axes when projecting the 3D virtual model from the 3D coordinate on to the 2D image; and
selecting rotation that yields a best match between the projection of the 3D virtual model and the patient's organ observed in the 2D image.

7. The method of claim 6, wherein the step of selecting is by a user via at least one of:
a visual inspection of each match, and
a quantitative measure automatically computed indicative of a degree of match between the projection of the 3D virtual model and the patient's organ observed in the 2D image.

8. Machine readable medium having information recorded thereon for estimating a three-dimensional (3D) coordinate of a 3D virtual model, wherein the information, when read by the machine, causes the machine to perform the following steps:
accessing a 3D virtual model constructed for an organ of a patient based on a plurality of images of the organ prior to a medical procedure;
obtaining a first pair of corresponding feature points, with a first two-dimensional (2D) feature point on the organ observed in a 2D image acquired during the medical procedure and a first corresponding 3D feature point from the 3D virtual model;
obtaining a second pair of corresponding feature points, with a second 2D feature point on the organ observed in the 2D image and a second corresponding 3D feature point from the 3D virtual model, wherein the depths of the first and the second 3D feature points are substantially the same; and
automatically determining a first 3D coordinate of the first 3D feature point and a second 3D coordinate of the second 3D feature point based on the first and the second pairs of corresponding feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

9. The medium of claim 8, wherein
the 3D virtual model has six degrees of freedom with first three degrees of freedom related to the 3D coordinate having values along X, Y, Z axes of a camera coordinate system; and
a depth corresponding to Z value of the 3D coordinate is on a line of sight of the first 2D feature point that has a 2D coordinate with respect to an image coordinate system.

10. The medium of claim 9, wherein the 3D virtual model has second three degrees of freedom related to rotations of the 3D virtual model with respect to each of the X, Y, and Z axes.

11. The medium of claim 9, wherein the line of sight is formed between the first 2D feature point and a focal point of a camera associated with a medical instrument deployed in the medical procedure.

12. The medium of claim 10, wherein the first 3D coordinate of the first 3D feature point and the second 3D coordinate of the second 3D feature point are determined based on:

$$\begin{bmatrix} X_1 \\ Y_1 \\ Z_1 \end{bmatrix} = M_{camera} \begin{bmatrix} x_1 \\ y_1 \\ 1 \end{bmatrix} \cdot s_1$$

$$\begin{bmatrix} X_2 \\ Y_2 \\ Z_2 \end{bmatrix} = M_{camera} \begin{bmatrix} x_2 \\ y_2 \\ 1 \end{bmatrix} \cdot s_1$$

where $(X_1, Y_1, Z_1)$ and $(X_2, Y_2, Z_2)$ are respectively three values along X, Y, Z axes for the first and the second 3D coordinates, $(x_1, y_1)$ and $(x_2, y_2)$ are respectively the image coordinates of the first and the second 2D feature points, and $s_1$ is a scaling factor along the line of sight corresponding to depth Z, which, when the first and the second 3D feature points have substantially the same depth, can be solved from $$d = \left\| M_{camera} \left( \begin{bmatrix} x_1 \\ y_1 \\ 1 \end{bmatrix} - \begin{bmatrix} x_2 \\ y_2 \\ 1 \end{bmatrix} \right) \right\| s_1$$

where d on the left side represents the second distance and the expression on the right side represents the first distance and $M_{camera}$ is a matrix representing camera parameters obtained via camera calibration.

13. The medium of claim 10, wherein the information, when read by the machine, further causes the machine to perform the step of determining the second three degrees of freedom via:
    adjusting rotation of the 3D virtual model with respect to at least one of the X, Y, and Z axes when projecting the 3D virtual model from the 3D coordinate on to the 2D image; and
    selecting a rotation that yields a best match between the projection of the 3D virtual model and the patient's organ observed in the 2D image.

14. The medium of claim 13, wherein the step of selecting is by a user via at least one of:
    a visual inspection of each match, and
    a quantitative measure automatically computed indicative of a degree of match between the projection of the 3D virtual model and the patient's organ observed in the 2D image.

15. A system for estimating a three-dimensional (3D) coordinate of a 3D virtual model, comprising:
    an anatomical structure mesh generation unit configured for constructing a 3D virtual model for an organ of a patient based on a plurality of images of the organ prior to a medical procedure; and
    a one-mark based model-to-video alignment unit configured for
        obtaining a first pair of corresponding feature points, with a first two-dimensional (2D) feature point on the organ observed in a 2D image acquired during the medical procedure and a first corresponding 3D feature point from the 3D virtual model,
        obtaining a second pair of corresponding feature points, with a second 2D feature point on the organ observed in the 2D image and a second corresponding 3D feature point from the 3D virtual model, wherein the depths of the first and the second 3D feature points are substantially the same, and
        automatically determining a first 3D coordinate of the first 3D feature point and a second 3D coordinate of the second 3D feature point based on the first and the second pairs of corresponding feature points so that a first distance between the determined first 3D coordinate and the determined second 3D coordinate equals to a second distance between a first actual 3D coordinate of the first 3D feature point and a second actual 3D coordinate of the second 3D feature point in the 3D virtual model.

16. The system of claim 15, wherein
    the 3D virtual model has six degrees of freedom with first three degrees of freedom related to the 3D coordinate having values along X, Y, Z axes of a camera coordinate system; and
    a depth corresponding to Z value of the 3D coordinate is on a line of sight of the first 2D feature point that has a 2D coordinate with respect to an image coordinate system.

17. The system of claim 16, wherein the line of sight is formed between the first 2D feature point and a focal point of a camera associated with a medical instrument deployed in the medical procedure.

18. The system of claim 16, wherein the first 3D coordinate of the first 3D feature point and the second 3D coordinate of the second 3D feature point are determined based on:

$$\begin{bmatrix} X_1 \\ Y_1 \\ Z_1 \end{bmatrix} = M_{camera} \begin{bmatrix} x_1 \\ y_1 \\ 1 \end{bmatrix} \cdot s_1$$

$$\begin{bmatrix} X_2 \\ Y_2 \\ Z_2 \end{bmatrix} = M_{camera} \begin{bmatrix} x_2 \\ y_2 \\ 1 \end{bmatrix} \cdot s_1$$

where $(X_1, Y_1, Z_1)$ and $(X_2, Y_2, Z_2)$ are respectively three values along X, Y, Z axes for the first and the second 3D coordinates, $(x_1, y_1)$ and $(x_2, y_2)$ are respectively the image coordinates of the first and the second 2D feature points, and $s_1$ is a scaling factor along the line of sight corresponding to depth Z, which, when the first and the second 3D feature points have substantially the same depth, can be solved from $$d = \left\| M_{camera} \left( \begin{bmatrix} x_1 \\ y_1 \\ 1 \end{bmatrix} - \begin{bmatrix} x_2 \\ y_2 \\ 1 \end{bmatrix} \right) \right\| s_1$$

where d on the left side represents the second distance and the expression on the right side represents the first distance and $M_{camera}$ is a matrix representing camera parameters obtained via camera calibration.

19. The system of claim 15, further comprising a patient-mesh-based global and local camera pose computation and optimization unit configured for
    adjusting rotation of the 3D virtual model with respect to at least one of the X, Y, and Z axes when projecting the 3D virtual model on to the 2D image at the 3D coordinate; and
    selecting a rotation that yields a best match between the projection of the 3D virtual model and the patient's organ observed in the 2D image.

20. The system of claim 19, wherein the best match is determined by a user via at least one of:
    a visual inspection of each match, and
    a quantitative measure automatically computed indicative of a degree of match between the projection of the 3D virtual model and the patient's organ observed in the 2D image.

* * * * *